US008690918B1

(12) United States Patent
Williams (10) Patent No.: US 8,690,918 B1
(45) Date of Patent: Apr. 8, 2014

(54) SPINOUS PROCESS FUSION REDUCTION PLATE FOR LUMBAR SPINE

(75) Inventor: Lytton Ade-Kunle Williams, Rolling Hills Estates, CA (US)

(73) Assignee: Onike Technologies, Dana Point, CA (US)

( * ) Notice: Subject to any disclaimer, the term of this patent is extended or adjusted under 35 U.S.C. 154(b) by 0 days.

(21) Appl. No.: 13/311,542

(22) Filed: Dec. 5, 2011

Related U.S. Application Data

(60) Provisional application No. 61/419,506, filed on Dec. 3, 2010, provisional application No. 61/480,349, filed on Apr. 28, 2011.

(51) Int. Cl.
*A61B 17/70* (2006.01)

(52) U.S. Cl.
USPC ............................. 606/248; 606/280; 606/286

(58) Field of Classification Search
USPC .......................................... 606/70, 246–299
See application file for complete search history.

(56) References Cited

U.S. PATENT DOCUMENTS

| | | | | |
|---|---|---|---|---|
| 3,648,691 A * | 3/1972 | Lumb et al. | .................... | 606/279 |
| 4,554,914 A * | 11/1985 | Kapp et al. | .................... | 606/86 A |
| 5,730,743 A * | 3/1998 | Kirsch et al. | ................... | 606/284 |
| 5,951,557 A * | 9/1999 | Luter | ............................. | 606/286 |
| 6,312,431 B1 * | 11/2001 | Asfora | ......................... | 606/279 |
| 6,364,881 B1 * | 4/2002 | Apgar et al. | ................... | 606/284 |
| 6,364,883 B1 * | 4/2002 | Santilli | ......................... | 606/279 |
| 7,048,736 B2 * | 5/2006 | Robinson et al. | ........... | 606/86 B |
| 7,335,203 B2 * | 2/2008 | Winslow et al. | .............. | 606/249 |
| 7,789,898 B2 * | 9/2010 | Peterman | ...................... | 606/279 |
| 7,875,061 B2 * | 1/2011 | Bolger et al. | .................. | 606/280 |
| 2003/0040746 A1 * | 2/2003 | Mitchell et al. | ................. | 606/61 |
| 2003/0187441 A1 * | 10/2003 | Bolger et al. | ................... | 606/69 |
| 2006/0116681 A1 * | 6/2006 | Bert | ................................. | 606/69 |
| 2007/0270812 A1 * | 11/2007 | Peckham | ........................ | 606/61 |
| 2009/0264927 A1 * | 10/2009 | Ginsberg et al. | ............. | 606/246 |
| 2010/0262193 A1 * | 10/2010 | Frigg et al. | .................... | 606/281 |

\* cited by examiner

*Primary Examiner* — Jerry Cumberledge (57) ABSTRACT

A spinal device in which a plate is placed on both sides of the lamina spinous process. The plates include horizontal and diagonal slots through which anchoring screws may be placed and secured. The screws may pass through the base of the spinous process and lamina structure. The plates may have cut-out portions on the ventral side to accommodate the lamina when reduction is performed. The diagonal slots preferably have an apex proximate to the dorsal side and open at the ventral side. The two plates can be mirror images of each other, and, when secured together by the screws, forms a stable construct that can sandwich the spinous process.

19 Claims, 8 Drawing Sheets

SPINOUS PROCESS FUSION REDUCTION PLATE FOR LUMBAR SPINE

CROSS-REFERENCES TO RELATED APPLICATIONS

This application claims priority from provisional U.S. Application No. 61/419,506, filed Dec. 3, 2010 and provisional U.S. Application No. 61/480,349, filed Apr. 28, 2011, each incorporated by reference in its entirety.

FIELD OF THE INVENTION

The present invention relates generally to orthopedic devices. More specifically, the present invention relates to orthopedic devices for the spinous process.

BACKGROUND

Spinal surgery is a common medical procedure in the United States and throughout the world. Spinal surgery is typically performed to decompress nerves and/or to stabilize the spinal elements. Spinal surgery can involve either anterior or posterior approaches to the spine. There are variations in the spinal anatomy of the cervical, thoracic, and lumbar levels of the spine. However, there are common anatomical elements of the spine at all the levels. The anterior bone elements of the spine include the vertebral bodies, with the interposed intervertebral discs. The posterior bone elements of the spine include the lamina, the spinous processes, the facet joints, the pedicles, and the transverse processes. Several ligaments, including the anterior longitudinal ligament, the posterior longitudinal ligament, the ligamentum flavum (or interlaminar ligament) and the interspinous ligament provide fibrous connections between the bone elements and contribute to the mechanical stability of the spine.

The spinous process of a vertebra is directed backward and downward from the junction of the laminae, and serves for the attachment of muscles and ligaments. The spinous process may be described as the protrusion on the center of the back of a vertebral body. The spinous process is the bone that can be felt down one's back. The paired transverse processes are oriented 90 degrees to the spinous process and provide attachment for back muscles.

Spondylolisthesis is a condition in which a bone (vertebra) in the lower part of the spine slips out of the proper position onto the bone below it, such as an anterior slip of a vertebrae in relation to the vertebrae immediately below it. In degenerative spondylolisthesis, the forward translation of the vertebral body may also cause narrowing of the central spinal canal at the level of the slip. The narrowing of the canal in degenerative spondylolisthesis has been referred to as the "napkin ring effect." An illustrative description as one imagines the spinal canal as a series of napkin rings with one of the rings slid forward in comparison to the others. Subluxation of the upper adjacent vertebrae to the one below it may cause degenerative spondylolisthesis. The levels generally involved in the pathology include 90% at L4-L5, and 8% at L3-L4 and 2% at L5-S1. The degree of subluxation is less than 50% (grade 1 to 2) without surgery.

Degenerative spondylolisthesis may occur in older patients over forty years of age, and in more prevalent in patients over the age of sixty. Aging degenerative may show changes in the interverebral disc of the two vertebra adjacent to each other and the posterior articular process of the facet joints. Degenerative spondylolisthesis also is more common in females than males, and degenerative spondylolisthesis is more common in diabetes patients.

The translation of one vertebra and the other may present with symptoms of stenosis. The disc protrudes posteriorly into the vertebral canal. This may be referred to as a pseudo-herniated disc because of the slip. Degenerative spondylolisthesis may present with symptoms of neurologic claudication with lumbar spine pain, thigh pain, cramping from prolonged standing or walking. Treatments may include bracing, anti-inflammatory steroids, and physical therapy. Surgery including surgical fusion also may be employed to stabilize the segment and decompress the spine. There is a need for a cost-effective treatment that avoids the contraindications of other treatments.

SUMMARY OF THE INVENTION

Briefly and in general terms, the present invention provides a spinous process device in which a plate is placed on both sides of the lamina spinous process. The plates may include horizontal and diagonal slots through which anchoring screws may be placed and secured. The screws may pass through the base of the spinous process and lamina structure. The plates may have cut-out portions on the ventral side to accommodate the lamina when reduction is performed. When secured together by the screws, the plates can sandwich the spinous process in a stable construct.

In one aspect, the spinal device comprises a first plate having a dorsal side and ventral side, the first plate being substantially flat and having an elongated shape. The plate may further have a substantially horizontal slot and a substantially diagonal slot, wherein the substantially diagonal slot is proximate to a cut-out portion on the ventral side of the first plate, and the cut-out portion being configured to accommodate the lamina; a second plate configured as a substantially mirror image of the first plate, wherein the horizontal slots and diagonal slots of the first plate and the second plate are sized so as to accommodate anchoring screws such that when the first plate and the second plate is secured together by the screws, wherein the spinous process is stabilized by being sandwiched between the first plate and the second plate.

Other features and advantages of the invention will become more apparent from the following detailed description of preferred embodiments of the invention, when taken in conjunction with the accompanying exemplary drawings.

DETAILED DESCRIPTION OF THE PREFERRED EMBODIMENTS

Figure 1:
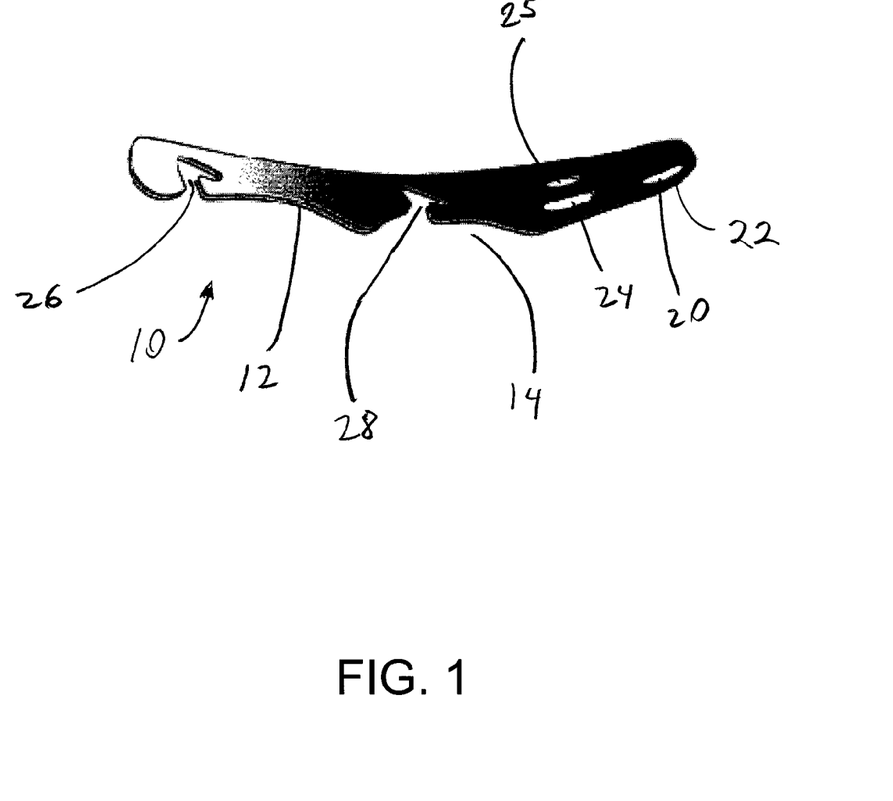
FIG. 1 is a perspective view of one embodiment of the invention showing an elongated plate and slots formed therein.

As illustrated in FIG. 1, in general terms, the present invention provides a new and improved spinal process device. Although described herein for application to the spine, application to other bony anatomic structures is also contemplated. The concept behind the plate and screws through the spinous process was derived for its simplicity, ease of use and time constraints with minimal complications. Prior intra spinous technology has potential drawbacks such as screw loosening, difficulty in properly fitting the plate to the spine, too high placement of the plate, and canal penetration with the screws.

Other spinous process techniques include the use of the spinous process for fixation of the spine and fusion of the spine with the Triple Bowman wire technique with cortical cancellous bone strips and wires through the spinous process. Another technique used the Drummond buttons, wires and rods to fix the spine in the cervical, thoracic and lumbar spine.

Figure 2:
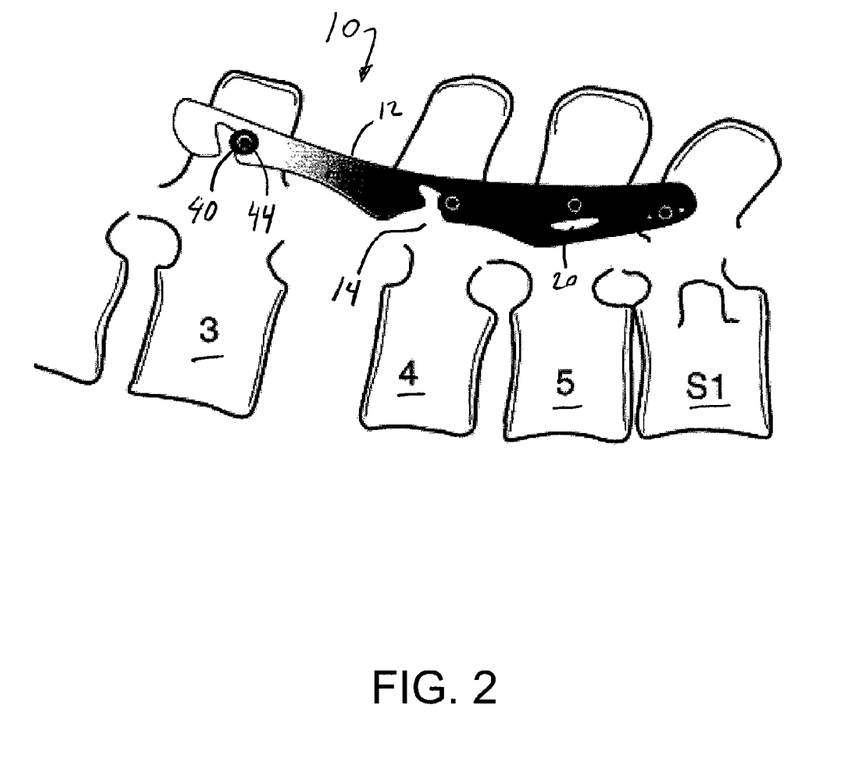
FIG. 2 is a side view of one embodiment of the invention showing an elongated plate and slots formed therein anchored to the spine.

As illustrated in, for example, FIGS. 1 and 2, one embodiment of the spinous process device 10 has an elongated wedge-like shape. The spinous process device 10 may consist of two plates 12 (only one is shown in FIG. 1) which are mirror images of each other. The plate 12 has slots 20 formed therein which receive bone screws 40 or other fasteners. The slots may include substantially horizontal slots 22, 24, 25 and a substantially diagonal slots 26, 28. The substantially diagonal slot 28 is proximate to a cut-out portion 14 on the ventral side of the first plate 12, and the cut-out portion may be configured to accommodate the lamina or other structure. The diagonal slot 26 is near the top end of the plate 12. The substantially horizontal slots 22, 24, 25 are towards the bottom end of the plate 12. A second plate (not shown) may be configured as a substantially mirror image of the first plate 12. The horizontal slots and diagonal slots of the first plate and the second plate are sized so as to accommodate anchoring screws 40 such that when the first plate and the second plate is secured together by the screws 40 and nuts 44, as illustrated in FIG. 2. Preferably the horizontal slot is bounded, and the diagonal slot may have one end open to the ventral side of the plate. The substantially diagonal slots preferably include at least one secondary slot branching away from the apex of the diagonal slot. The apex is preferably located proximate to the dorsal side of the plate.

The two plates, which are mirror images of one another, may extend from L3 to the sacrum. The plates may be lordotic and wedge-shaped. The dorsal end is preferably thick or relatively thicker, and the volar end narrow or relatively narrow with a flare to match the shape of the base of the spinous process and top of the lamina. From the cephalad direction the plates preferably are wider, and preferably narrower caudally. In one embodiment, there are two horizontal slotted holes on the plate for the L5 and S1 vertebral spinous process lamina structure. In the embodiment, there are two diagonal slotted holes from dorsal to ventral at level L3 and L4, and there are two extended slots at L4 and one slot at L3 angling back caudally from the diagonal slots. These slots preferably are made to fit three or four mm screws which are used to anchor the plates to the vertebra for in-situ fusion or to stabilize and/or minimally reduce the unstable L4 or L3. When the screws are secured, the two plates sandwich the spinous process lamina to stabilize it. In the alternative, one may secure fixation of the plate using a slot placed at the L5 spinous process using two horizontal slots over the plates L5 spinous process.

Figure 3:
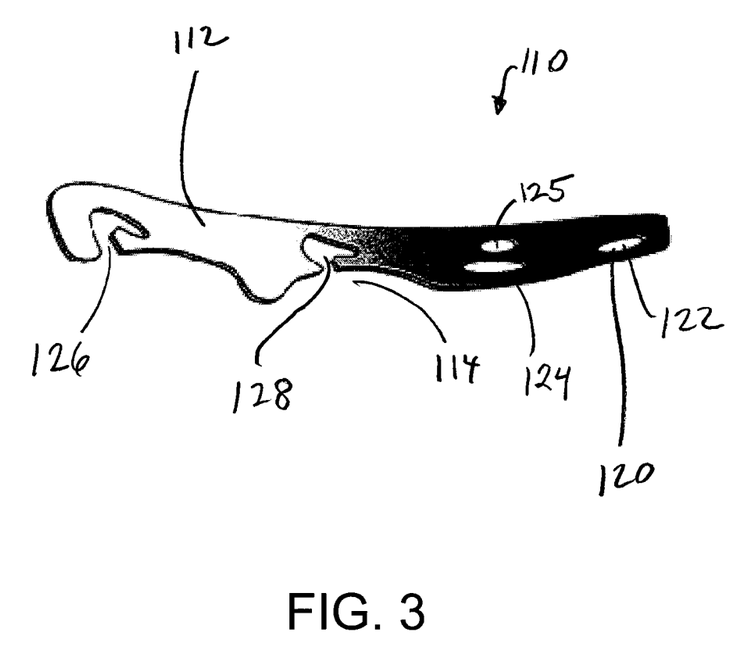
FIG. 3 is a perspective view of a second embodiment of the invention showing an elongated plate and slots formed therein.
Figure 4:
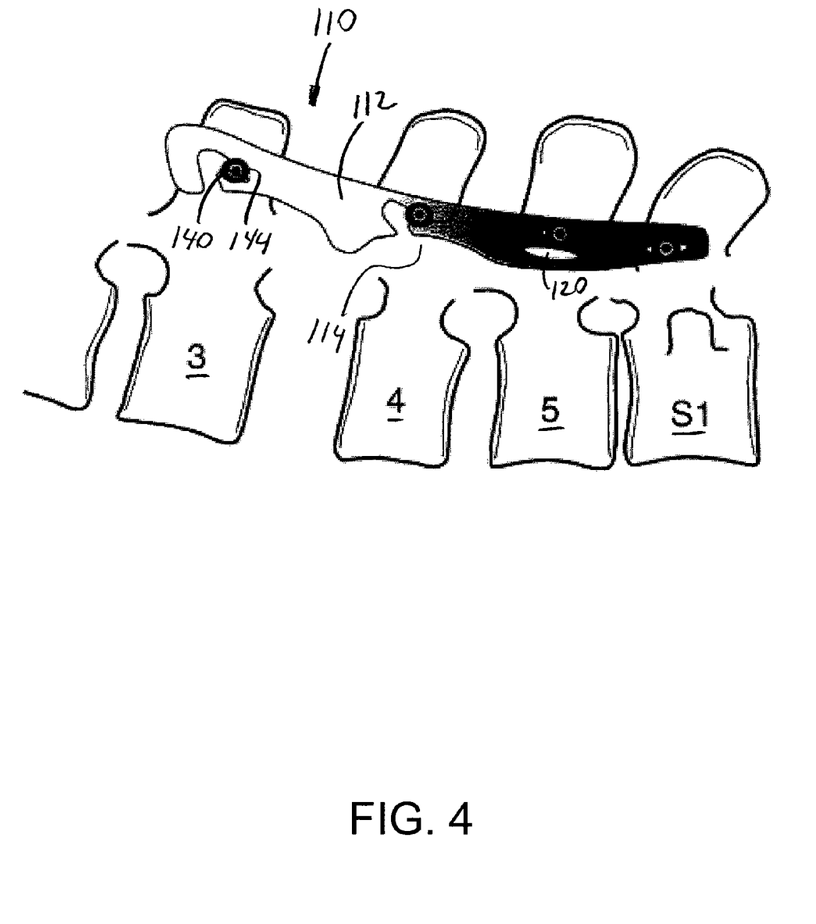
FIG. 4 is a side view of the second embodiment of the invention showing an elongated plate and slots formed therein anchored to the spine.

In another second embodiment, as illustrated in FIGS. 3 and 4, the spinous process device 100 comprising the plate 112 with slots 120 (horizontal slots 122, 124 and 125, and diagonal slots 126 and 128) may be used for spinal reduction. The horizontal slots 122, 124, 125 are bounded located towards the bottom end of the plate, and the diagonal slots 126, 128 are open to the ventral side, and diagonal slots 126 is located near the top end of the plate. The diagonal slot 128 is proximate to a cut-out portion 114 on the ventral side.

The fusion reduction plates can be used at one level L4 or two levels L3 and L4. The reduction plates has cut outs over the lamina of L3 and L4 to accommodate the lamina when reduction is performed. The diagonal slots over L4 and L3 have at least one slot at the height of the diagonal slot going caudally for four or five mm. This allows one to anchor the screws on the vertebra to the plates when the spine is reduced. The volar end of the slot at L3 and L4 is open, this is for the reduction screw to gain access to the slot in the plates.

A hole may be made in the base of the spinous process on both sides to allow a screw to pass through and a nut is placed on the other side. Preferably, the plate 112 at L5 is fixed first, and possibly the sacrum as well, with screw 140 and nuts 144. A screw at L4 may then be used to reduce the unstable spine or spondylo by compressing bilaterally. The screw may slide up the slot on the plate and may be tightened in place when the screw lands on the slot pointing backward. Such a configuration is intended to stop the spine from sliding back down. A stable construct may be created by tightening the screw and the nuts to the plate and spinous process.

After the distraction the volume of the canal will increase, the facet joints between L4-L5 will be distracted, and if L3 is reduced, the facet joints between L3-L4 will also be distracted and open. Now fusion can be done with facet screw fixation. After the distraction reduction, there is room for lumbar decompression by doing a laminotomy.

Figure 5:
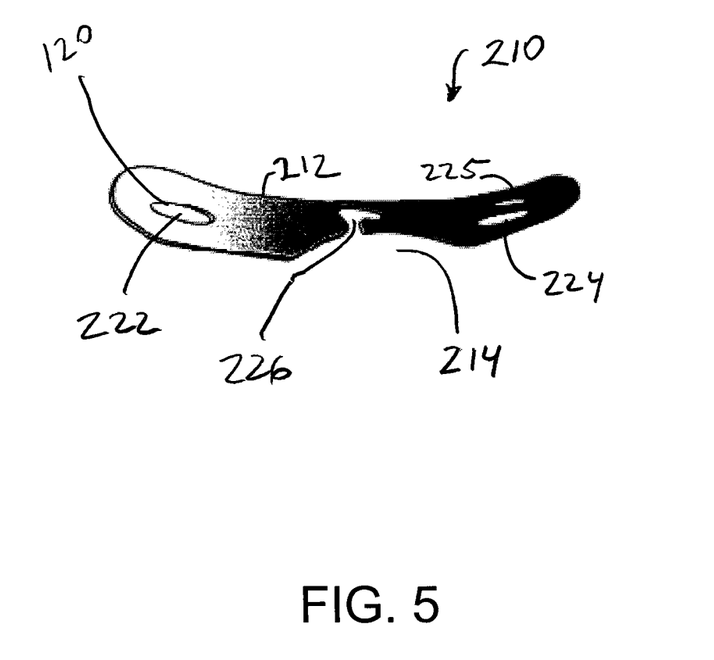
FIG. 5 is a perspective view of a third embodiment of the invention showing an elongated plate and slots formed therein.
Figure 6:
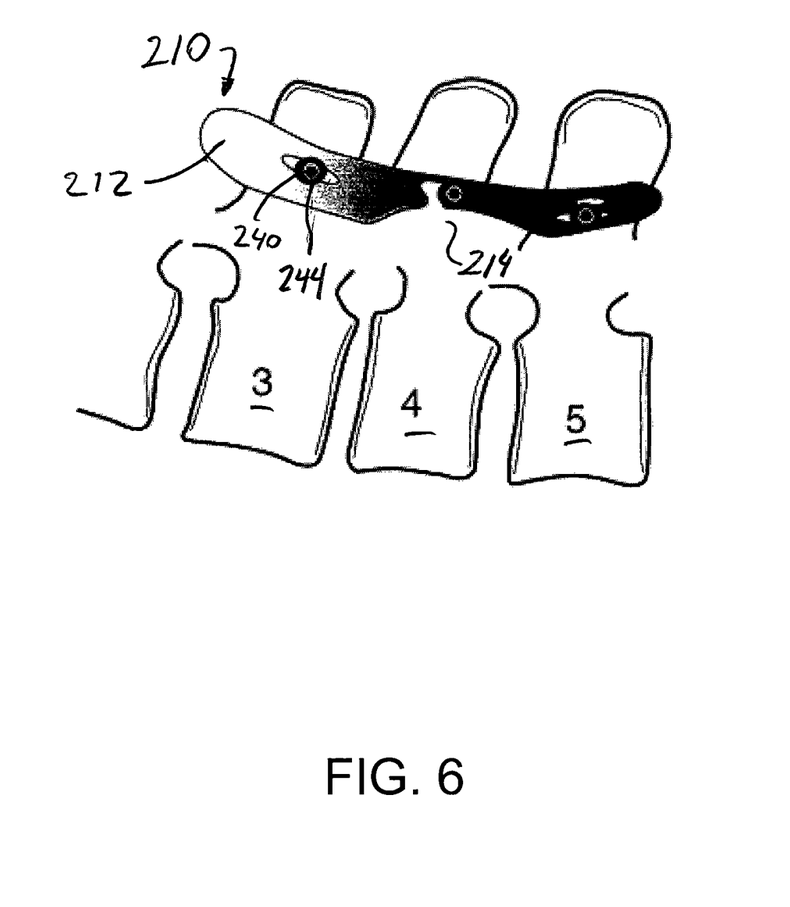
FIG. 6 is a side view of the third embodiment of the invention showing an elongated plate and slots formed therein anchored to the spine.

Yet another third embodiment of the plate is for one level distraction reduction at L4-L5 degenerative spondylolisthesis is illustrated in FIGS. 5 and 6. The spinous process device 210 preferably comprises the plate 212 with slots 220 (horizontal slots 222, 224 and 225 located near both the top and bottom ends of the plate 212, and at least one diagonal slot 226 open to the ventral side adjacent a cut-out portion 214). Here L4 is lower than L5, and the plates 212 preferably are first fixed to L5 and L3 bilaterally with double fixation of plate at the L5 process. Screws 240, such as four mm screws, are inserted through the base of the L4 spinous process. Now distract reduce the spondy by compressing the plate with screw 240 being directed into the slot 214 on the plate over L4 vertebra. The construct may be fixed by tightening the nuts 244 on the screw 240 to sandwich the spinous process. The volume of the canal will increase to indirectly decompress the canal. The facet joints will be distracted and open, then screw fixation of the joints can be done thus obtaining fusion.

Figure 7:
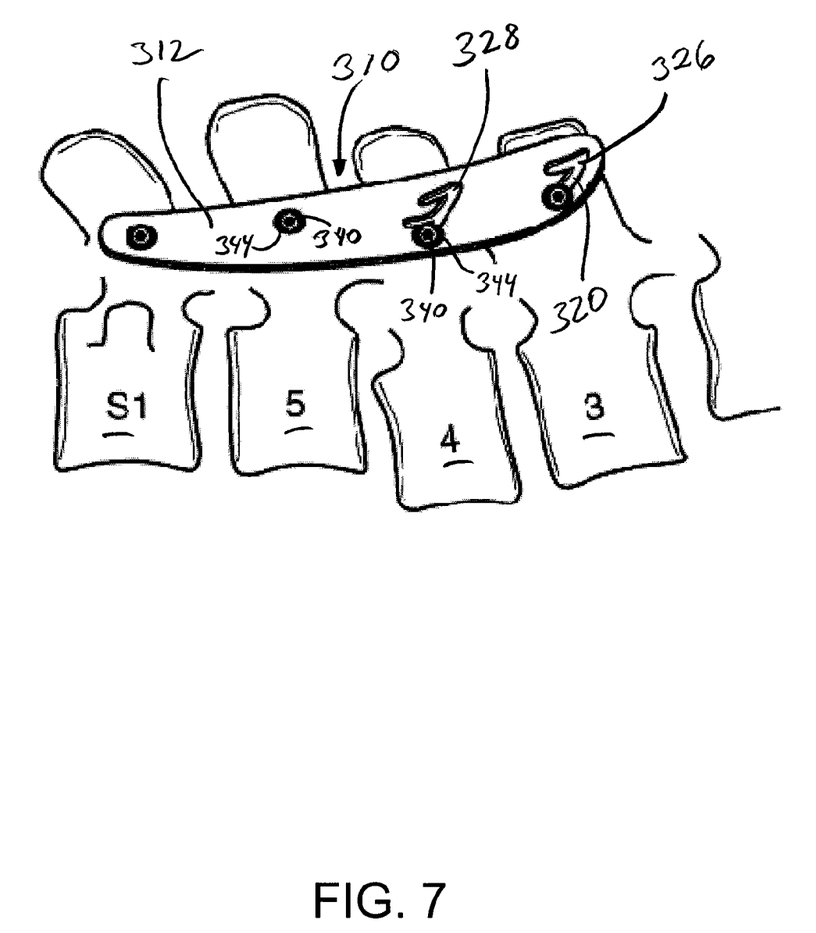
FIG. 7 is a side view of a fourth embodiment of the invention showing an elongated plate and slots formed therein anchored to the spine.
Figure 8:
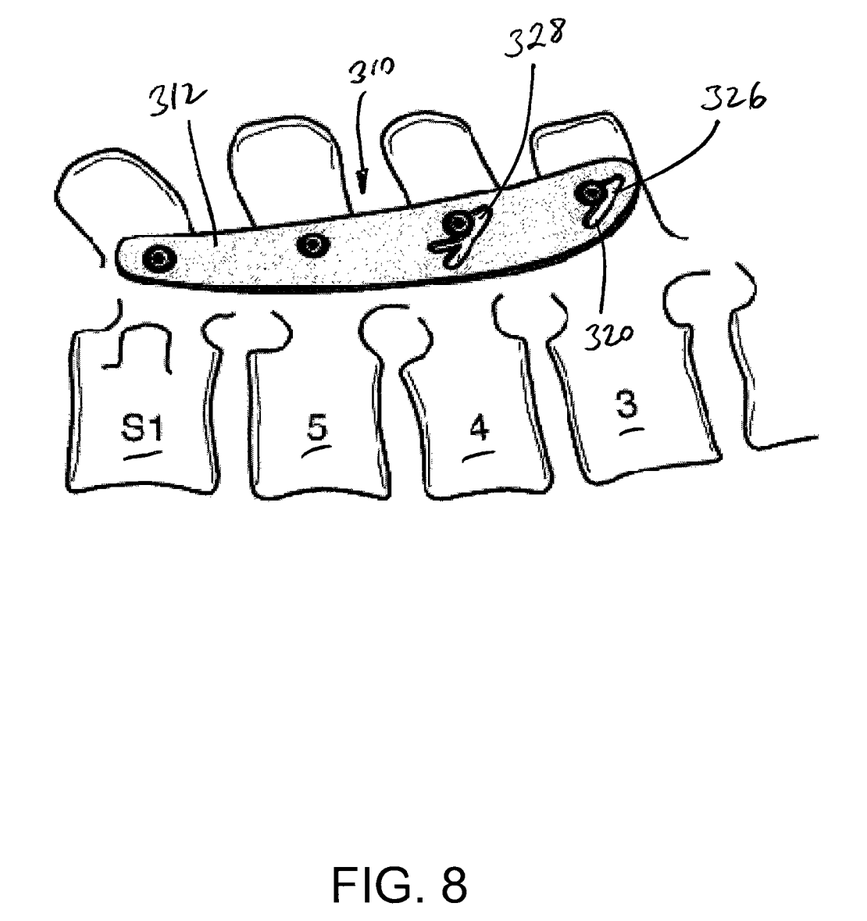
FIG. 8 is a side view of the fourth embodiment of the invention showing an elongated plate and anchored to the spine at a new location along the slots.

Another alternative embodiment of the spinous process device 310 and plate 312 is illustrated in FIGS. 7 and 8. In this embodiment, the diagonal slots 326 and 328 are bounded. The substantially diagonal slots may preferably include at least a secondary slot branching away from the apex, which is located proximate to the dorsal side of the plate. An additional secondary slot may branch away closer to the midpoint of the diagonal slot. After the screws 340 are secured by the nuts 344, the bone may be placed at different locations along the branched diagonal slot. FIG. 7 illustrates unreduced spondylolisthesis with the spinous process plate 312 inserted, and FIG. 8 illustrates reduced spondylolisthesis with the spinous process plate 312.

In the new intra lamina spinous process reduction technique discussed herein, it is preferable that two plates on both sides of the lamina spinous process are used with screws going through the plates on both sides of the base of the spinous process, lamina structure and the plate on the other side and then the nuts are used to secure the construct. This can be done from L3 to the sacrum. One use of this device is for reduction, stabilization and fusion of degenerative spondylolisthesis and allowing for decompression of the segment and facet fusion. It can also be used for stabilization and in-situ fusion of the segment.

The embodiments described therefore are to be considered in all respects as illustrative and not restrictive. Although the present invention has been described in terms of certain preferred embodiments, other embodiments will be apparent to those of ordinary skill in the art. Accordingly, the scope of the invention is intended to be defined only by reference to the appended claims.

The invention claimed is:

1. A spinal device comprising:
   a first plate having a dorsal side and ventral side, the first plate being substantially flat and having an elongated shape, and further having a substantially horizontal slot branching off from a substantially diagonal slot, wherein the substantially diagonal slot is proximate to a cut-out portion on the ventral side of the first plate, and the cut-out portion being configured to accommodate the lamina;
   a second plate configured as a substantially mirror image of the first plate, wherein the horizontal slots and diagonal slots of the first plate and the second plate are sized so as to accommodate anchoring screws such that when the first plate and the second plate is secured together by the screws, the spinous process is stabilized by being sandwiched between the first plate and the second plate.

2. The spinal device of claim 1, wherein the substantially diagonal slots of the first plate and the second plate, each have an apex proximate to the dorsal side and the substantially diagonal slots are open to the ventral side.

3. The spinal device of claim 1, wherein the substantially diagonal slots of the first plate and the second plate, each have at least one secondary slot branching away.

4. The spinal device of claim 1, wherein the substantially diagonal slots of the first plate and the second plate, each have an apex proximate to the dorsal side and the substantially diagonal slots are open at the ventral side, and further including a secondary slot branching away from the apex.

5. The spinal device of claim 1, wherein the substantially diagonal slots are located on one end of the first plate and the second plate, and the substantially horizontal slots are bounded and located on the other end of the first plate and the second plate.

6. The spinal device of claim 1, wherein the substantially diagonal slots are and located on one end of the first plate and the second plate, and the substantially horizontal slots are bounded and located on the other end of the first plate and the second plate, and wherein the substantially diagonal slots of the first plate and the second plate, each have an apex proximate to the dorsal side and open at the ventral side.

7. The spinal device of claim 1, wherein the substantially diagonal slots are and located on one end of the first plate and the second plate, and the substantially horizontal slots are located on the other end of the first plate and the second plate, and wherein the substantially diagonal slots of the first plate and the second plate, each have an apex proximate to the dorsal side and open at the ventral side, and further including a secondary slot branching away from the apex.

8. The spinal device of claim 1, wherein the substantially horizontal slots are bounded and located on the opposite ends of the first plate and the second plate, and the substantially diagonal slots are located between the horizontal slots on the opposite ends of the first plate and the second plate.

9. The spinal device of claim 1, wherein the substantially horizontal slots are bounded and located on the opposite ends of the first plate and the second plate, and the substantially diagonal slots are located between the horizontal slots on the opposite ends of the first plate and the second plate, and wherein the substantially diagonal slots of the first plate and the second plate, each have an apex proximate to the dorsal side and open at the ventral side, and further including a secondary slot branching away from the apex.

10. A method of using a spinous process device, comprising the steps of:
    placing on one side of a spinous process, a first plate having a dorsal side and ventral side, the first plate being substantially flat and having an elongated wedge-like shape, and further having a bounded, substantially horizontal slot branching off from a substantially diagonal slot, wherein the substantially diagonal slot is proximate to a cut-out portion on the ventral side of the first plate, and the cut-out portion being configured to accommodate the lamina;
    placing on the other side of the spinous process, a second plate configured as a substantially mirror image of the first plate, wherein the horizontal slots and diagonal slots of the first plate and the second plate are sized so as to accommodate anchoring screws;
    inserting a first anchoring screw through the horizontal slot of the first plate, through the spinous process, and through the horizontal slot of the second plate;
    securing the first anchoring screw;
    inserting a second anchoring screw through the diagonal slot of the first plate, through a hole made in the spinous process, and through the diagonal slot of the second plate;
    securing the second anchoring screw to create a stable construct.

11. The method of claim 10, wherein the substantially diagonal slots of the first plate and the second plate, each have an apex proximate to the dorsal side.

12. The spinal device of claim 10, wherein the substantially diagonal slots of the first plate and the second plate, each have at least one secondary slot branching away.

13. The spinal device of claim 10, wherein the substantially diagonal slots of the first plate and the second plate, each have an apex proximate to the dorsal side and the substantially diagonal slots are open at the ventral side, and further including a secondary slot branching away from the apex.

14. The spinal device of claim 10, wherein the substantially diagonal slots are located on one end of the first plate and the second plate, and the substantially horizontal slots are bounded and located on the other end of the first plate and the second plate.

15. A spinal device comprising:
    a first plate having a dorsal side and a ventral side, the first plate being substantially flat and having an elongated shape, and further having a hooked slot comprising a substantially horizontal slot branching off from a diagonal slot wherein a secondary slot branches off from the diagonal slot;

a second plate configured to be secured to the first plate by anchoring screws engaging the hooked slot of the first plate, wherein a spinous process is stabilized by being sandwiched between the first plate and the second plate.

16. The spinal device of claim 15, wherein the diagonal slot is open to the ventral side.

17. The spinal device of claim 15, wherein the orientation of the substantially horizontal slot of the first plate generally follows a longitudinal axis of the first plate, and the diagonal slot has an orientation which transects the longitudinal axis of the first plate.

18. The spinal device of claim 15, wherein the hooked slot is proximate to a cut-out having a concave portion on the ventral side of the first plate, and the cut-out being configured to accommodate lamina of a vertebra.

19. The spinal device of claim 15, wherein the substantially horizontal slot forms an acute angle with the diagonal slot.

* * * * *